United States Patent [19]
Castleman et al.

[11] 4,119,851
[45] Oct. 10, 1978

[54] APPARATUS AND A METHOD FOR DETECTING AND MEASURING TRACE GASES IN AIR OR OTHER GAS BACKGROUNDS

[75] Inventors: B. Wayne Castleman, Largo; Bernard C. Schluter, Clearwater, both of Fla.

[73] Assignee: Honeywell Inc., Minneapolis, Minn.

[21] Appl. No.: 809,219

[22] Filed: Jun. 23, 1977

[51] Int. Cl.² ............................................. G01T 1/18
[52] U.S. Cl. ................................. 250/382; 250/384
[58] Field of Search ............... 250/382, 384, 385, 379

[56] References Cited
U.S. PATENT DOCUMENTS

| | | | |
|---|---|---|---|
| 3,573,460 | 4/1971 | Skala | 250/383 |
| 3,835,328 | 9/1974 | Harris et al. | 250/432 |
| 3,853,750 | 12/1974 | Volsy | 250/432 |
| 3,892,968 | 7/1975 | Lovelock | 250/384 |

*Primary Examiner*—Harold A. Dixon
*Attorney, Agent, or Firm*—Albin Medved

[57] ABSTRACT

Method and apparatus for detecting the presence of very small concentrations of certain vapors and gases in air or other gaseous backgrounds. A gas sample is ionized by a source of ionizing radiation. The sample of ionized gas is then directed through a recombination region where ions are selectively recombined. The ionized gas is further directed through a drift region where the ions are subjected to a drift potential and separated into different groups, depending upon their mobilities. In an alternate embodiment, the ionized gas is first directed through a drift region, followed by a recombination region.

14 Claims, 2 Drawing Figures

APPARATUS AND A METHOD FOR DETECTING AND MEASURING TRACE GASES IN AIR OR OTHER GAS BACKGROUNDS

BACKGROUND OF THE INVENTION

This invention relates to apparatus for detection of small amounts of selected vapors or gases in an atmosphere of air or other gas. The invention combines the features of an ionization cell and a drift tube, attaining advantages of both and producing a result which is superior to that produced by either one of them by itself.

The design and operating problems of ionization cells are set forth in U.S. Pat. No. 3,835,328. Such cells can be used to detect the presence of small concentrations of a selected group of chemical vapors or gases in the air or in other vapors or gas backgrounds. U.S. Pat. No. 3,835,328 describes an ionization detector in which a gas sample flows past a source of ionization radiation and through a recombination region to a ion collection region. In the ion collection region a current is produced as a function of the ion concentration in the gas sample. By providing a sufficiently long path and exposure to adequate surface, the recombination of ions is enhanced and controlled in such a way that ion concentration remaining in the gas or vapor sample when it reaches the collection region is a function of trace gases or vapors in the sample. A characteristic of the ionization cell is that the signal is dependent on both the stability of the ions which are formed and upon their concentration. Thus, the cell responds to some interfering vapors or gases as well as to the vapors or gases of interest, even though the size and mobility of interfering ions may be considerably different. An improved ionization cell is disclosed in U.S. patent application Ser. No. 754,148, filed Dec. 27, 1976.

In a drift tube, vapors or gases are subjected to ionizing radiation in the same manner as in the ionization cell. In a drift tube, however, the resulting ions are placed in an electric field, causing the ions to migrate in a predetermined direction, where different types of ions can be separated, detected, and measured by virtue of the difference of velocity or mobility of the ions in an electric field. Ion shutter grids or gates are provided for segregating the ions in accordance with their drift time.

SUMMARY OF THE INVENTION

To improve the selectivity, such that only vapors or gases of interest will be detected, the apparatus according to the present invention combines the features of an ionization cell and a drift tube. The invention can take form in two basic configurations. In one configuration, the ionization cell operates as a pre-selector or pre-filter which eliminates or reduces the effects of the great majority of possible interfering ion species while allowing a significant fraction of the ions of interest to pass through. The drift tube then receives the selected ions and further classifies the ions on the basis of their mobility.

In the preferred embodiments of the present invention the ionization cell is similar to that which is described in co-pending patent application Serial No. 754,148. The ions which emerge from the ionization cell are carried into the drift tube section by the continuous flow of gas provided by the action of a downstream pump. The ions pass through a ground potential screen which prevents the collector of the ionization cell from being influenced by the potentials of the drift tube. A first gate controls the flow of ions into the drift region and accelerates the ions with a DC potential which establishes a linear potential gradient in the region of the tube for an appropriate period of time. The potential gradient causes the ions to drift to a selector collector at different rates, depending upon their mobilities. The result is that ions of different mobilities become separated into distinct groups. The group of ions of interest is allowed to pass a timing gate by application of a proper signal and is then collected by the selector collector. Groups of interfering ions are prevented from reaching the collector by closing the timing gate.

In the alternate configuration of the present invention, the drift tube section is located upstream from the ionization cell. The ions formed by a radioactive source are directed through a drift tube which selects only ions of a specific mobility and allows them to pass into the ionization cell region, where further selection is accomplished. The ions exiting the drift tube section and those reaching the collector of the ionization cell can be measured separately. The signals thus generated can be used individually or logically combined for increased selectivity.

The apparatus according to the present invention has the advantages over the prior art in that it has better selectivity than either the ionization cell or the drift tube alone. One section acts as a pre-filter for the other section, which reduces the response to many undesired vapors or gases.

A further advantage of the present invention is that it provides an apparatus which is more sensitive than the ionization cell by itself since the practical sensitivity of the ionization cell depends to a large extent on its response to interferences. Another advantage of the present invention is that only a single ionization source is required for the operation of both the ionization cell and drift tube. These and further objects will become apparent to those skilled in the art upon inspection of the following specification, claims, and drawings.

DESCRIPTION OF THE PREFERRED EMBODIMENT

Figure 1:
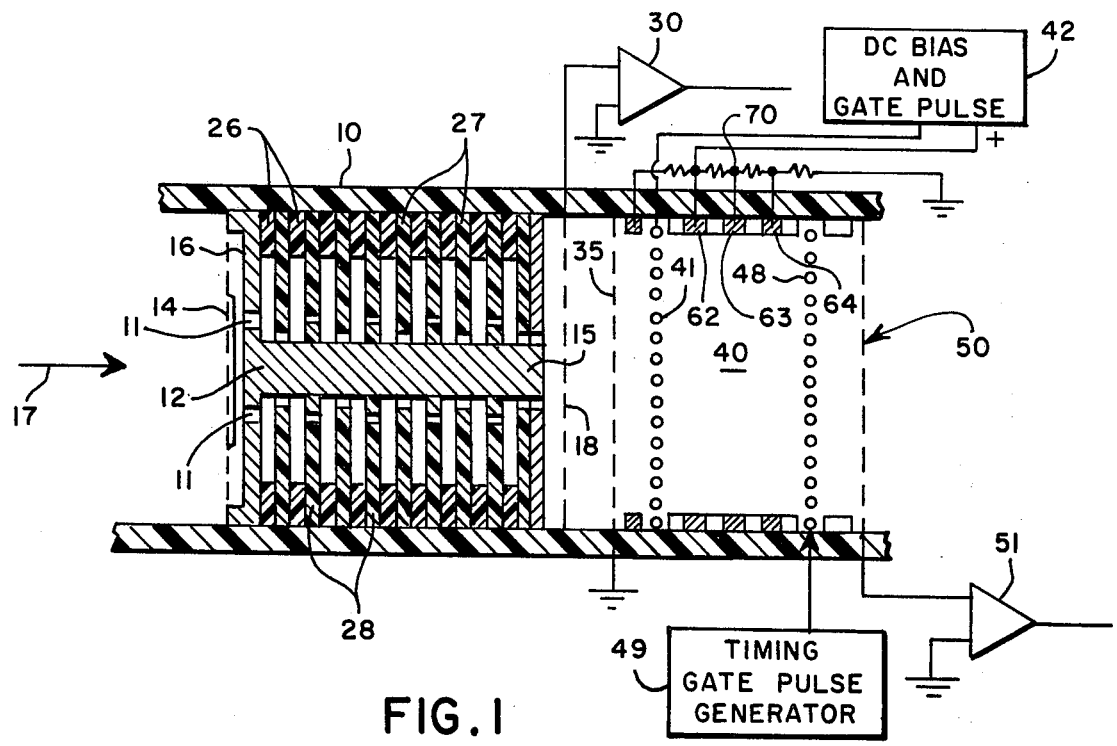
FIG. 1 illustrates a preferred embodiment of the present invention with the ionization cell upstream from the drift tube.

Referring to FIG. 1, a preferred embodiment of the present invention is shown having a housing 10 constructed of a non-conductive material, such as Teflon. Mounted within the housing, at a first end, is a radiation emitting source 14, which consists of a metal screen to which is affixed a radiation emitting foil. A manifold 12, constructed of a conductive material, and consisting of a circular flange 16 corresponding in size to the internal cross-sectional dimension of housing 10, and a metal stud 15 protruding from the flange axially along housing 10, is positioned adjacent to radiation emitting source 14. The flange portion of manifold 12 contains a number of apertures 11, which provide the passages for gas from radiation source 14 into a recombination region.

Gas sample, such as air, enters housing 10 as shown by arrow 17, impinging on radiation source 14, where the gas is ionized. Beyond radiation source 14, the gas sample enters a recombination region through apertures 11 in manifold 12. The recombination region is comprised of a series of washers 26 and baffles 27 and 28, as shown in FIG. 1, and as described in U.S. Pat. No. 3,835,328. The series of washers and baffles provide an extended path which enhances ion recombination by exposing ions to a large surface area. The washers and baffles of the recombination region are constructed of non-conductive material, such as Teflon.

The downstream end of the recombination region is defined by an electrically conductive collector screen 18, which is connected to the input of an amplifier 30.

The ions which pass through the recombination region are carried into a drift region 40 by continuous flow of gas provided by the action of a downstream pump (not shown). The ions pass a ground plane screen 35, the function of which is to prevent collector screen 18 from being influenced by the potentials generated in the drift region. An electrical grid 41, connected to receive signals from a DC bias and gate pulse generator 42, forms a first gate at which potentials can be applied to allow or to prevent ions from entering into the drift region. The upstream end of drift region 40 is defined by ground plane screen 35 and conductive grid 41 comprised of a plurality of conductive wires, and the downstream end of the drift region is defined by a selector collector 50. An electrical grid 48 is positioned on the upstream side of selector collector 50. The region between grids 41 and 48 has a plurality of conductive rings 62, 63, 64 which are connected to a source of electric DC potential via voltage divider network 70 to establish a linear electric field between grids 41 and 48. Grid 48 is connected to receive a signal from a timing gate pulse generator 49 and can be controlled to allow passing of the specific group of ions of interest to be collected by selector collector 50. The group of interfering ions are prevented from reaching selector collector 50 by opening timing gate 49 just long enough to allow only the ions of interest to pass. The signal generated at selector collector 50 is amplified by amplifier 51 to provide an indication of the concentration in the gas sample of specific ions of interest. The signal from amplifier 51 can be used alone or it can be logically combined with the signal from amplifier 30 for increased selectivity.

The signals applied to grids 41 and 48 are of the type well known in the prior art. They may be derived from standard pulse, sine or square wave generators. Generally, for co-planar grids, such as 41 and 48, an average potential is applied to the grid conductors which is equal to the potential of the drift tube in the region of the grid. To transmit ions, the two sides of each grid are connected to the same potential. To capture ions, the grid conductors are held at a potential difference with respect to each other, but at an average potential equal to the drift tube potential at that location. When square or sine wave signals are used, the frequency determines which species of ions are collected. When pulses are used to operate the gates, the width of the pulse determines the resolution and sensitivity of the drift tube, while the delay time between pulses determines the species which is to be transmitted through the gates.

Figure 2:
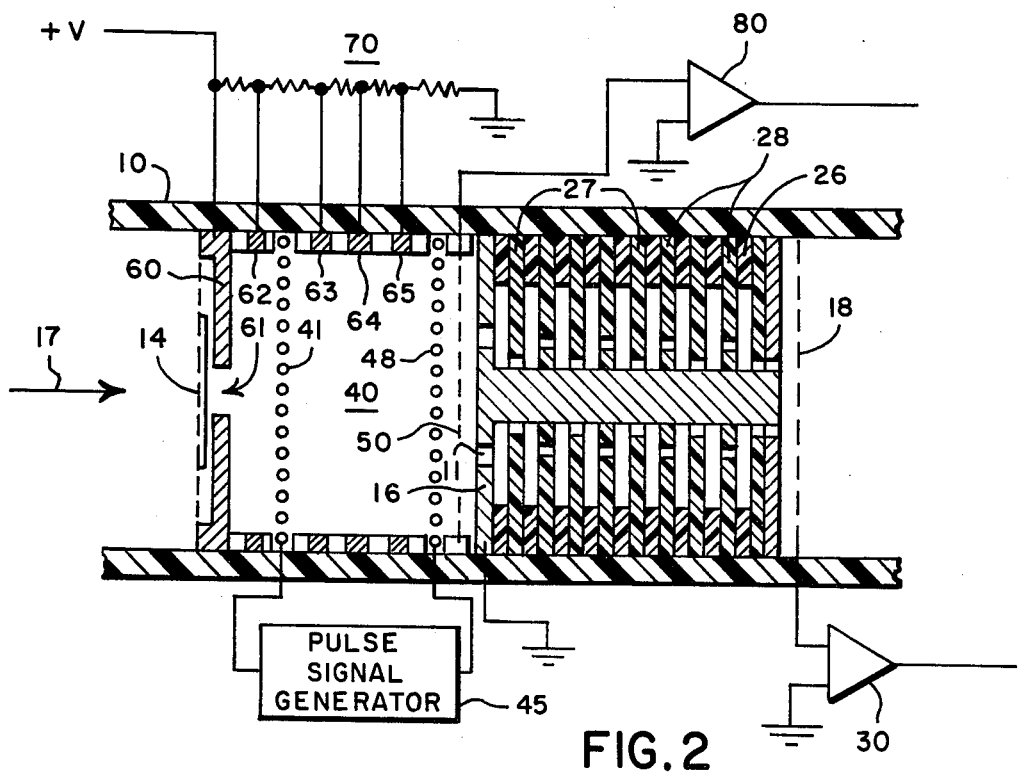
FIG. 2 illustrates an alternate preferred embodiment of the present invention with the drift tube upstream from the ionization cell.

An alternate embodiment of the present invention is shown in FIG. 2. The difference of the apparatus of FIG. 2, as compared to that of FIG. 1, is that the drift region is located upstream from the recombination region. For clarity of understanding, the reference numerals used in connection with FIG. 1 are used also in FIG. 2 to identify corresponding elements. Radiation emitting source 14 is positioned at the upstream end of housing 10 where the gas sample is received from the direction shown by arrow 17. A conductive plate 60, having a central opening 61, separates radiation source 14 from drift region 40. The other end of drift region 40 (the downstream end) is defined by manifold 16, which also defines the upstream end of the recombination region. A plurality of conductive rings 62, 63, 64 and 65 are mounted within drift region 40 and are connected to a source of electric potential via voltage divider network 70 to establish a linear electric field between plate 60 and manifold 16. Electrically conductive grids 41 and 48 act as electrical shutters which, upon receiving an appropriate signal from pulse signal generator 45 allows only ions of a specific mobility to pass through the drift region and into the recombination region beyond manifold 16.

The selected ions which are allowed to pass through drift region 40 are then further acted upon in the recombination region by interaction with the surfaces created by washers 26 and baffles 27 and 28 and manifold 16. The ions exiting drift region 40 generate a signal at collector 50 which is received at the input of amplifier 80. The ions passing through the recombination region and reaching collector 18 at the downstream end of the recombination region generate a signal which is applied to the input of amplifier 30. The amplified signals from amplifiers 30 and 80 may be used individually as an indication of the presence of specific ions in the gas sample, or these signals can be logically combined for increased selectivity.

In another mode of operation of either previously described embodiment illustrated in FIGS. 1 and 2, the grid voltages on grids 41 and 48 are held at constant values instead of being supplied with pulse, sine, or square wave signals. The alternate wires of each grid are held at different constant potentials such that a fraction of the ions are collected by each of the grids while the remaining ions pass through and are either collected by the collector 50 in the apparatus of FIG. 1 or pass into the manifold 16 in the apparatus of FIG. 2. In this mode of operation, the grid potentials act upon the ions as the ions pass between the wires of the grid. The ions with higher mobilities can move more easily to the wires and are collected, whereas ions of lower mobilities pass through the grids without being collected. In this way the grids act as low ion mass filters since they allow heavier ions to pass and be measured, while stopping the lighter ions.

A unique and improved apparatus for sensing and measuring gaseous impurities has been shown and described in the foregoing specification. Various modifications of the inventive concepts will be obvious to those skilled in the art, without departing from the spirit of the invention. It is intended that the scope of the invention be limited only by the following claims.

What is claimed is:

1. Apparatus for detecting trace amounts of vapors or gases in air or other gaseous backgrounds, said apparatus comprising:
   a housing defining a passage for flow of gas between an input and an output;
   a source of ionizing radiation positioned in said passage near said input for creating ions in said gas;
   a recombination region defined by first portion of said passage between said source of ionizing radiation and said output, said recombination region including means for facilitating recombination of ions in said gas entering the recombination region, and means for measuring the number of ions remaining in the gas leaving the recombination region;

a drift region defined by a second portion of said passage between said source of ionizing radiation and said output, said drift region including a collector electrode, means for establishing a drift potential for causing said ions to drift toward said collector electrode, gating means for allowing only ions of predetermined mobility to reach said collector electrode, and means for measuring the number of ions reaching said collector electrode.

2. Apparatus according to claim 1, wherein said recombination region is defined at the end nearest said source of ionizing radiation by an electrically conductive manifold mounted within said passage and at the end furthest from said source of ionizing radiation by a collector screen at which an electric signal is generated as a function of the number of ions present in the gas after passing through the recombination region; and wherein said means for facilitating recombination of ions includes a plurality of baffles constructed of electrically insulative material mounted between said manifold and said collector screen, said baffles each having a plurality of apertures and being spaced from each other to allow passage of gas therethrough and therebetween.

3. Apparatus according to claim 1, wherein said means for establishing a drift potential in said drift region includes:

a conductive plate at the end nearest said source of ionizing radiation and a plurality of parallel electrically conductive rings encircling the drift region and spaced from each other and from said conductive plate by insulative means, and a voltage divider network for connecting the conductive plate and the rings to a source of potential to establish a linear electric field between said conductive plate and said collector electrode.

4. Apparatus according to claim 1, wherein said gating means includes a pair of electrically conductive grids mounted within said drift region, said grids being positioned in a spaced relationship and being operable to act as electrical shutters in response to application of an electrical signal.

5. Apparatus according to claim 1, wherein said gating means includes a pair of electrically conductive grids mounted within said drift region and positioned in a spaced relationship, said grids each comprising a plurality of conductors, the alternate of said conductors of each grid being connected to a first potential, while the remaining of said conductors being connected to a second potential, whereby ions of higher mobilities are collected by said grids, and ions of lower mobilities pass through said grids.

6. Apparatus according to claim 1, wherein said recombination region is located in said passage between said source of ionizing radiation and said drift region, and said drift region is located between said recombination region and said output.

7. Apparatus according to claim 6, wherein said recombination region is defined at the end nearest said source of ionizing radiation by an electrically conductive manifold mounted within said passage and at the end furthest from said source of ionizing radiation by a collector screen at which an electric signal is generated as a function of the number of ions present in the gas after passing through the recombination region; and wherein said means for facilitating recombination of ions includes a plurality of baffles constructed of electrically insulative material mounted between said manifold and said collector screen, said baffles each having a plurality of apertures and being spaced from each other to allow passage of gas therethrough and therebetween.

8. Apparatus according to claim 6, wherein said means for establishing a drift potential in said drift region includes:

a conductive plate at the end nearest said source of ionizing radiation and a plurality of parallel electrically conductive rings encircling the drift region and spaced from each other and from said conductive plate by insulative means, and a voltage divider network for connecting the conductive plate and the rings to a source of potential to establish a linear electric field between said conductive plate and said collector electrode.

9. Apparatus according to claim 8, wherein said gating means includes a pair of electrically conductive grids mounted within said drift region, said grids being positioned in a spaced relationship and being operable to act as electrical shutters in response to application of an electrical signal.

10. Apparatus according to claim 8, wherein said gating means includes a pair of electrically conductive grids mounted within said drift region and positioned in a spaced relationship, said grids each comprising a plurality of conductors, the alternate conductors of each grid being maintained at different constant potentials, such that a fraction of ions are collected by each of said grids, while the remaining ions pass through said grids.

11. Apparatus according to claim 1, wherein said drift region is located in said passage between said source of ionizing radiation and said recombination region, and said recombination region is located between said drift region and said output.

12. Apparatus according to claim 11, wherein said recombination region is defined at the end nearest said source of ionizing radiation by an electrically conductive manifold mounted within said passage and at the end furthest from said source of ionizing radiation by a collector screen at which an electric signal is generated as a function of the number of ions present in the gas after passing through the recombination region; and wherein said means for facilitating recombination of ions includes a plurality of baffles constructed of electrically insulative material mounted between said manifold and said collector screen, said baffles each having a plurality of apertures and being spaced from each other to allow passage of gas therethrough and therebetween.

13. Apparatus according to claim 11, wherein said means for establishing a drift potential in said drift region includes:

a conductive plate at the end nearest said source of ionizing radiation and a plurality of parallel electrically conductive rings encircling the drift region and spaced from each other and from said conductive plate by insulative means, and a voltage divider network for connecting the conductive plate and the rings to a source of potential to establish a linear electric field between said conductive plate and said collector electrode.

14. Apparatus according to claim 13, wherein said timing gate includes a pair of electrically conductive grids mounted within said drift region, said grids being positioned in a spaced relationship and being operable to act as electrical shutters in response to application of an electrical signal.

* * * * *